United States Patent [19]

Abe

[11] Patent Number: 4,912,216
[45] Date of Patent: Mar. 27, 1990

[54] METHOD FOR PRODUCTION OF PERFLUORO-(N-VINYLAMINE) COMPOUNDS

[75] Inventor: Takashi Abe, Kasugai, Japan

[73] Assignees: Agency of Industrial Science & Technology; Ministry of International Trade & Industry, Tokyo, Japan

[21] Appl. No.: 71,774

[22] Filed: Jul. 10, 1987

[30] Foreign Application Priority Data

Jul. 15, 1986 [JP] Japan ................. 61-166887
Jul. 15, 1986 [JP] Japan ................. 61-166889

[51] Int. Cl.$^4$ .................. C07C 85/24; C07C 87/26; C07C 223/04; C07C 265/30
[52] U.S. Cl. .................. 540/484; 544/106; 544/358; 546/184; 548/400; 564/468; 564/510; 564/509; 562/849; 562/850
[58] Field of Search ............. 540/484; 544/106, 358; 546/184; 548/400; 564/468, 510, 509; 260/544 F; 562/849, 850

[56] References Cited

U.S. PATENT DOCUMENTS

| | | | |
|---|---|---|---|
| 3,091,643 | 5/1963 | Wiley | 570/136 X |
| 3,326,984 | 6/1967 | Anderson et al. | 260/544 F |
| 3,467,638 | 9/1969 | Pattison | 260/544 F |
| 3,641,104 | 2/1972 | Anderson et al. | 260/544 F |
| 4,474,700 | 10/1984 | Krespan | 260/544 F |
| 4,782,148 | 11/1988 | Abe | 540/484 |

FOREIGN PATENT DOCUMENTS

| | | | |
|---|---|---|---|
| 0194825 | 11/1983 | Japan | 570/136 |
| 0022773 | 1/1987 | Japan | 544/358 |
| 02022756 | 1/1987 | Japan | 548/400 |

Primary Examiner—Mukund J. Shah
Assistant Examiner—Diana G. Rivers
Attorney, Agent, or Firm—Oblon, Spivak, McClelland, Maier & Neustadt

[57] ABSTRACT

A perfluoro-(N-vinylamine) compound containing a $>NCF=CF_2$ group is produced from a perfluoro-compound containing a group of the general formula:

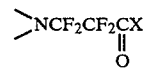

(wherein X stands for a fluorine atom or a —OM group having an alkali or alkaline earth metal ion for M) and having connected to the group of the general formula a perfluoro-alkyl group having a total of 2 to 6 carbon atoms contained in the main carbon chain thereof by heating the perfluoro-compound at a temperature in the range of 100° C. to 500° C. thereby effecting conversion of the group of the foregoing general formula into the aforementioned $>NCF=CF_2$ group.

6 Claims, No Drawings

METHOD FOR PRODUCTION OF PERFLUORO-(N-VINYLAMINE) COMPOUNDS

BACKGROUND OF THE INVENTION

This invention relates to a novel method for the production of perfluoro-(N-vinylamine) compounds. More particularly, this invention relates to a method for producing, economically in high yields from readily available raw materials, perfluoro-(N-vinylamine) compounds which are useful as intermediates or macromolecular monomers for synthesis of fluorine-containing products such as surfactants, agricultural pesticides, and medicines.

In the perfluoro-(N-vinylamine) compounds represented by the following general formula:

(I)

[wherein $R_1$ and $R_2$ independently stand for a perfluoro-alkyl group, providing that the two groups may be coupled either directly or through the medium of an oxygen atom or a nitrogen atom and the two groups may form a five-member or six-member ring in combination with the nitrogen atom to which they are coupled] and a perfluoro-alkyl amino group is joined to either of the carbon atoms of a double bond. By using these perfluoro-(N-vinylamine) compounds as intermediates, therefore, various useful compounds containing the perfluoro-alkyl amino group can be produced.

By copolymerizing these compounds with other fluoro-olefins, it is possible to lower the degree of crystallinity of producing copolymers due to the incorporation of the bulky perfluoro-alkylamino group and allow them to acquire improved mechanical properties. These perfluoro-(N-vinylamine) compounds are highly useful as intermediates for synthesis and as sources for production of fluorine-containing polymers.

These perfluoro-(N-vinylamine) compounds have already been known to the art and have heretofore been produced by the following two methods.

The first method comprises subjecting a perfluoroalkyl amino radical and a suitable fluorine-containing olefin to addition reaction and subsequently subjecting the resultant adduct to a reaction for removal of hydrogen halogenide or a reaction for thermal decomposition thereby re-forming an unsaturated bond.

It is known that perfluoro-(N,N-dimethylvinylamine) (specification of U.S. Pat. No. 3,311,599), perfluoro(N-vinylmorpholine) ["Journal of Chemical Society, Perkin I., page 5 (1973)], and perfluoro-(N-vinylpiperidine) ["Journal of Chemical Society", (C), page 2608 (1968)] can be produced by this first method.

Since this method uses special compounds as starting materials, however, it entails difficulty in procuring the raw materials, complexity of procedure of the production, and deficiency of yield as problems yet to be solved.

The second method comprises converting recently developed perfluoro-carboxylic acid derivatives into perfluoro-(N-vinylamine) compounds by thermal decomposition. Specifically, methods for producing perfluoro-(N-vinylamine) compounds represented by the formulas (Ia) and (Ib) by respectively using as raw materials perfluoro-carboxylic acid derivatives represented by the general formulas (II) and (III) have been known (Japanese Patent Application SHO 60(1985)-162631 and SHO 60(1985)-162632 and U.S. Ser. No. 06/886608, for example.

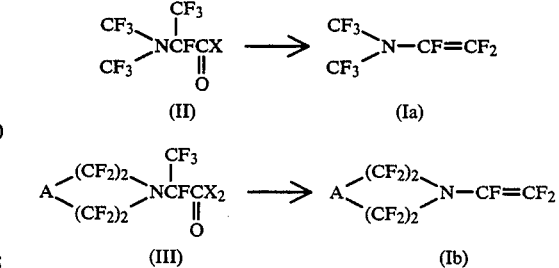

[wherein A stands for a chemical bond, $CF_2$, $O<$, or R—N (wherein R is a perfluoro-alkyl amino group), X has the same meaning as defined above, and $X_1$ stands for F, perfluoro-alkoxy group, or OM (wherein M has the same meaning as defined above)].

This second method, however, exclusively uses the perfluoro-carboxylic acid derivatives represented by the general formulas (II) and (III) as raw materials. No other perfluoro-carboxylic acid derivative has been known to be usable in the reaction which is effected by the second method.

SUMMARY OF THE INVENTION

An object of this invention is to provide a method for producing perfluoro-(N-vinylamine) compounds useful as intermediates for synthesis and as monomers for the manufacture of fluorine-containing polymers easily from readily available raw materials by the reaction of thermal decomposition.

This invention has been perfected as a result of a study continued for the accomplishment of the object described above.

To be specific, this invention is directed to a method for the production of a perfluoro-(N-vinylamine) compound containing a $>NCF=CF_2$ group from a perfluoro-compound containing a group of the following general formula:

[wherein X stands for one member selected from the group consisting of (a) a fluorine atom and (b) a —OM group (wherein M is one member selected from the group consisting of alkali metal ions and alkaline earth metal ions of a valency of one] and having connected to the aforementioned group a perfluoro-alkyl group having a total of 2 to 6 carbon atoms contained in the main carbon chain thereof by heating the perfluoro-compound to a temperature in the range of 100° C. to 500° C. thereby effecting conversion of the group of the general formula into the $>NCF=CF_2$.

DETAILED DESCRIPTION OF THE PREFERRED EMBODIMENTS

The method of this invention is not anticipated by prior art.

As indicated by the following reaction formulas, when perfluoro-(2-alkoxypropionyl fluorides) and alkali metal salts of acids thereof are thermally decomposed, they undergo a reaction of decarboxylation and give rise to perfluoro-vinyl ethers in high yields. On the other hand, it has been known that in the case of perfluoro-(3-alkoxypropionyl fluorides) and alkali metal salts of acids thereof, they only give tetrafluoro-ethylene and lower perfluorocarboxylic acid fluorides as products of thermal decomposition (Japanese Patent Publication SHO 39(1964)-26709).

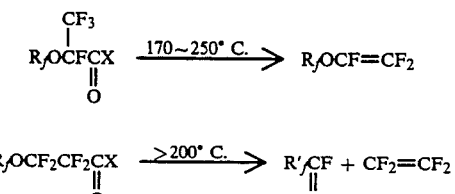

(wherein $R_f$ stands for a perfluoro-alkyl group of 1 to 8 carbon atoms, $R'_f$ for F or a perfluoro-alkyl group of 1 to 7 carbon atoms, and X has the same meaning as defined above).

In the case of perfluoro-(3-alkylamino group-substituted propionic acids) which are isoelectronic compounds relative to the perfluoro-(3-alkoxypropionic acids), therefore, it has been held that the acid fluorides and metal salts thereof will similarly undergo decomposition as shown by the following reaction formula.

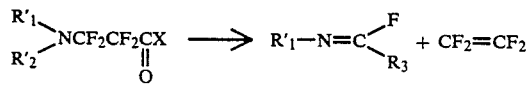

[wherein $R'_1$ and $R'_2$ independently stand for a perfluoroalkyl group of 1 to 5 carbon atoms, $R_3$ for a perfluoroalkyl group having one carbon atom less than $R'_2$, and X has the same meaning as defined above).

Thus, these perfluoro-(3-alkylamino group-substituted propionic acids) have never been contemplated as possible raw materials for the production of perfluoro(N-vinylamine) compounds.

The inventor took notice of the ready availability of perfluoro-(3-alkylamino group-substituted propionic acids) and continued a study in search of a method for the production of perfluoro-(N-vinylamine) compounds by using such propionic acids as raw materials. They consequently found unexpectedly that when these perfluoro-(3-alkylamino group-substituted propionic acids) are thermally decomposed, perfluoro-(N-vinylamine) compounds represented by the aforementioned general formula (I) are obtained as products of the thermal decomposition. This invention has been perfected as a result.

Concrete examples of the

group in the aforementioned general formula are as follows.

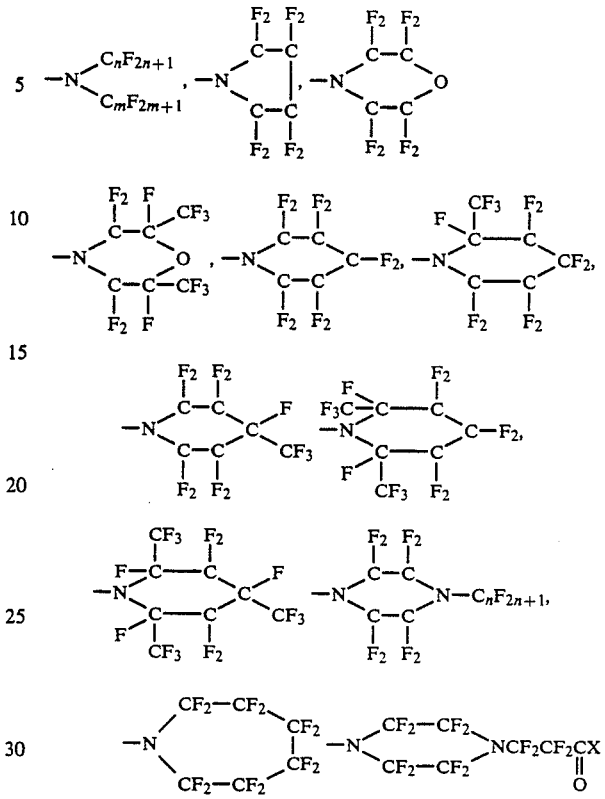

(where n and m independently stand for an integer in the range of 1 to 5).

In the method of this invention, perfluoro-compounds represented by the general formula (IV) described below are used as raw materials. Specifically, perfluoro-(3-alkylamino or 3-cyclicaminopropionyl fluorides) or alkali metal salts or alkaline earth metal salts of perfluoro-(3-alkylamino or 3-cyclicaminopropionic acids) are used.

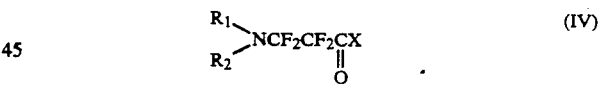

(wherein $R_1$, $R_2$ and X have the same meanings as defined above.)

The perfluoro-(3-alkylamino or 3-cyclic aminopropionyl fluorides) are easily obtained, for example, by electrolytically fluorinating a reactive derivatives of 3-alkylamino or 3-cyclicaminopropionic acids in liquid hydrogen fluoride (U.S. Pat. No. 3,471,484). The metal salts of perfluoro-(3-alkylamino or 3-cyclicaminopropionic acids are easily obtained by causing a hydroxide of an alkali metal or alkaline earth metal to react on the perfluoro-(3-alkylamino or 3-cyclic aminopropionyl fluorides) obtained as described above.

The perfluoro-(N-vinylamine) compounds of the general formula:

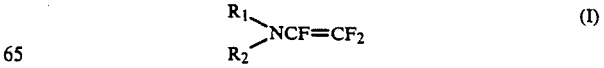

(wherein $R_1$ and $R_2$ have the same meanings as defined above) which is aimed at by the present invention is easily obtained by simply subjecting the perfluoro-compounds of the aforementioned general formula (IV) to thermal decomposition. In terms of the smoothness with which the reaction of thermal decomposition proceeds, preferred examples of the perfluoro-compounds to be used advantageously as the raw material include perfluoro-(3-alkylamino or 3-cyclic aminopropionyl fluorides), sodium salts of perfluoro-(3-alkylamino or 3-cyclicaminopropionic acids), and potassium salts of perfluoro-(3-alkylamino or 3-cyclicaminopropionic acids).

The temperature of the thermal decomposition is selected in the range of 100° C. to 500° C., preferably in the range of 100° C. to 300° C. If this temperature is unduly high, there tend to ensue secondary reactions such as unwanted decomposition. If it is unduly low, the conversion is obtained only in a low ratio. Though the time of reaction is variable with the reaction temperature, it is generally in the range of 10 seconds to two hours. The reaction time is short where a high reaction temperature is selected and is long where a low reaction temperature is selected.

The reaction pressure is not an important factor in this reaction of thermal decomposition. The reaction can be carried out effectively under a vacuum, normal atmospheric pressure, or an increased pressure. Preferably, the reaction is carried out under normal atmospheric pressure or under a vacuum because the product of the reaction can be recovered rather easily. The reaction of thermal decomposition, depending on the form of reaction, can be carried out using as a diluent for the reaction mixture either an inert gas such as nitrogen, helium, argon, or carbon dioxide or a non-protonic liquid compound such as a polyether, tetrachloroethylene, or n-heptane. In this case, the ratio of dilution is desired to be not more than 100 times the amount of the reaction mixture.

Further, for the sake of the reaction of thermal decomposition, it is essential that all the substances used in the reaction should contain no water.

Where perfluoro-(3-alkylamino or 3-cyclic-aminopropionyl fluorides) are used as the raw material in the method of this invention, the reaction of thermal decomposition is desired to be carried out in the presence of a metal salt or a metal oxide. In this case, the desired perfluoro-(N-vinylamine) compounds are obtained easily by continuously passing the raw material through a packed bed of the metal salt or metal oxide kept at a prescribed temperature thereby effecting the reaction of thermal decomposition. Though the method of the present invention is not very particular about the material for the reactor used for the thermal decomposition, the reactor is generally made of stainless steel or a Hastelloy metal. The packed bed mentioned above is not limited specifically by shape. It can be used effectively in any shape. Examples of the bed usable advantageously for the reaction include a fixed bed, a moving bed and a fluidized bed.

Concrete examples of the metal salt mentioned above include sodium carbonate, potassium carbonate, lithium carbonate, sodium phosphate, potassium phosphate, barium carbonate, calcium carbonate, magnesium carbonate, potassium sulfate, and sodium sulfate. As examples of the metal oxide, there can be cited zinc oxide and cadmium oxide. Among other metal compounds enumerated above, such solid salts as sodium carbonate and potassium carbonate prove to be particularly desirable because they are capable of decomposing the noxious $COF_2$ which occurs in the course of the thermal decomposition.

The method of this invention enables the perfluoro(N-vinylamine) compounds to be produced in a high yield through a very simple process from readily available raw materials. Thus, it constitutes an advantageous process for the production of the perfluoro-(N-vinylamine) compounds on a commercial scale.

Further, the perfluoro-(N-vinylamine) compounds produced by the method are used advantageously as an intermediate for the synthesis of fluorine-containing products such as surfactants, agricultural pesticides, and medicines and as a monomer for the production of fluorine-containing polymers.

Now, the present invention will be described more specifically below with reference to working examples. It should be noted that this invention is not limited in any way by these working examples.

EXAMPLE 1

As a raw material, a crude product obtained by electrolytically fluorinating methyl 3-dimethylaminopropionate and distilling the resultant product of fluorination to expel the greater part of low-boiling compounds was used. The perfluoro-(3-dimethylaminopropionyl fluoride) content of this crude product was 48.0% by weight.

In a three-neck flask having an inner volume of 200 ml and provided with a reflux condenser and a dropping funnel, 12.00 g of the crude product mentioned above [containing 5.75 g of perfluoro-(3-dimethylaminopropionyl fluoride)] and 30 ml of water were placed and phenolphthalein was added as an indicator thereto. The contents of the flask were kept agitated with a magnetic stirrer and ice cooled and a concentrated aqueous potassium hydroxide solution was added thereto dropwise until the resultant mixture showed alkalinity.

Then, the contents of the flask were transferred into a beaker having an inner volume of 300 ml and heated over a hot plate for evaporation of water. The residue was transferred into a flask having an inner volume of 200 ml and held therein under a vacuum at 70° C. for about eight hours for desiccation.

The white solid substance thus obtained in the flask was comminuted and, with a gas inlet tube connected to the upper end of the flask, helium gas was continuously supplied at a rate of 80 ml/min into the flask. The flask held in this state was heated in an oil bath to raise the temperature thereof gradually from 150° C. to 200° C. over a period of 60 minutes and the flask was then kept at the elevated temperature further for one hour to effect thermal decomposition of the reaction mixture held therein. The product of the thermal decomposition was condensed and collected in a trap kept cooled to −78° C. Thus, 4.53 g of fluorocarbon was collected.

This fluorocarbon was analyzed by gas chromatography [liquid phase: 1,6-bis(1,1,12-trihydroperfluorododecyloxy)-hexane, carrier: Chromosorb PAW 60 to 80 mesh, carrier gas: helium], IR, $^{19}$FNMR, and Mass. The data consequently obtained were found to agree with the spectroscopic data of known perfluoro-(N,N-dimethylvinyl amine).

The amount of perfluoro-(N,N-dimethylvinyl amine) thus obtained was 38.5 g and the yield thereof 86.0%.

EXAMPLE 2

The procedure of Example 1 was repeated, except that the cell drain product obtained by electrolytically fluorinating methyl 3-diethylaminopropionate was used in its unaltered form as a raw material. The cell drain product contained 83.4% by weight of perfluoro-(3-diethylaminopropionyl fluoride).

First, in a three-neck flask having an inner volume of 200 ml and provided with a reflux condenser and a dropping funnel, 50 ml of water was placed and kept cooled with ice and 32.61 g of the aforementioned cell drain product [containing 27.20 g of perfluoro-(3-diethylaminopropionyl fluoride)] was added dropwise. After completion of this dropwise addition, the resultant mixture was stirred for 50 minutes. Then, the solution consequently formed was neutralized with a concentrated aqueous solution of potassium hydroxide until the solution showed slight alkalinity. Then, the contents of the flask were transferred into a beaker having an inner volume of 300 ml and evaporated to dryness on a hot plate. Consequently, there was obtained 32.0 g of a white solid substance.

Then, in a mortar, this white solid substance and about 20 g of dry finely comminuted calcium fluoride added thereto were mixed and finely comminuted. The resultant fine powdered mixture was transferred into a round-bottomed flask having an inner volume of 200 ml, warmed to 80° C. over an oil bath and dried under a vacuum for one hour. The dry powder was thermally decomposed by being heated under a vacuum (110 mmHg) from 200° C. to 270° C. over a period of about 50 minutes and then kept at the elevated temperature further for 23 minutes. The fluorocarbon emanating from the thermally decomposed mixture was collected in a trap kept cooled at −78° C. As a result, 17.48 g of fluorocarbon was collected.

When the fluorocarbon was analyzed in the same manner as in Example 1, the amount of perfluoro-(N,N-diethylvinyl amine) thus produced was found to be 15.67 g and the yield thereof 69.0%.

The boiling point of this product was 56.0 to 57.0° C., $d_4^{20}$ thereof 1.6664, and $n_D^{20}$ thereof was <1.28. The spectroscopic data of this product were as follows.

$^{19}$F NMR data

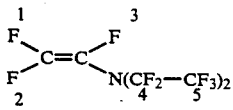

Chemical shift (ppm, based on CFCl$_3$)

1  −95.6 (d, d)
2  −107.8 (d, d)
3  −140.2 (d, d)
4  −95.9
5  −85.6

Coupling constant (Hz)
1 − 2 = 44
1 − 3 = 55
2 − 3 = 116

Data of mass analysis
m/z
333  M$^+$
314  [M−F]$^+$
264  C$_5$F$_{10}$N$^+$
195  C$_4$F$_7$N$^+$ Infrared absorption spectrum data
1808 cm$^{-1}$ (CF$_2$=CF−)

EXAMPLE 3

A tube of stainless steel 48.0 cm in length and 2.5 cm in inside diameter provided on the inlet side thereof with an instantaneous evaporator for gasification of raw material and a diluent gas flow regulator and on the outlet side thereof with a low-temperature trap was laid horizontally to serve as a reactor. In this reactor, 86.2 g of powdered sodium carbonate was placed so that the upper surface thereof would fall halfway of the height (diameter) of the tube, with either end of the cylinder sealed with metal wool.

First, the reactor was kept at 220° C. and helium gas was kept supplied thereto at a flow rate of 100 ml/min. Then, 7.17 g of a fluorocarbon mixture [having a perfluoro-(3-morpholinopropionyl fluoride) content of 71.5%] was supplied by the use of a fine metering pump to the instantaneous evaporator over a period of 55 minutes, there to be gasified and mixed with helium gas being introduced at a fixed flow rate. The resultant mixed gas was introduced into the reactor. The product of the reaction was condensed and collected in a trap kept cooled to −78° C.

As a result, there was obtained 4.47 g of fluorocarbon. When this fluorocarbon was analyzed in the same manner as in Example 1, it was found to contain 3.24 g of perfluoro-(N-vinylmorpholine). The conversion was 100% and the yield 76.7%.

EXAMPLE 4

The procedure of Example 2 was repeated, except that a fluorocarbon mixture constituting the cell drain product and having a perfluoro-(3-morpholinopropionyl fluoride) content of 70.3% by weight was used as a raw material.

By neutralizing 22.37 g of the fluorocarbon mixture [containing 15.7 g of perfluoro-(3-morpholinopropionyl fluoride)] with an aqueous potassium hydroxide solution and evaporating the neutralized fluorocarbon mixture to dryness, there was obtained 20.9 g of a white solid substance. By comminuting this solid substance and subjecting the comminuted substance to thermal decomposition under a vacuum, there was obtained 10.80 g of fluorocarbon. When this fluorocarbon was analyzed in the same manner as in Example 1, it was found to contain 1.00 g of perfluoro-(5,6-dihydro-2H-1,4-oxazine), and 9.80 g of perfluoro-(N-vinylmorpholine) (Yield 84.4%).

EXAMPLE 5

In the same reactor as used in Example 2, the procedure of Example 2 was repeated, except that 84.4 g of powdered sodium carbonate was packed in the reactor and a fluorocarbon mixture (cell drain product) having a perfluoro-(3-pyrollidinopropionyl fluoride) content of 71.7% was used as a raw material.

When 5.15 g of this fluorocarbon mixture was supplied to the reactor and thermally decomposed therein over a period of 27 minutes, 3.56 g of fluorocarbon was obtained in the cooled trap. When this fluorocarbon was analyzed in the same manner as in Example 1, it was found to contain 2.31 g of perfluoro-(N-vinylpyrrolidine). The conversion was 100% and the yield 76.5%.

EXAMPLE 6

In the same reactor as used in Example 2, the procedure of Example 2 was repeated, except that 84.4 g of powdered potassium carbonate was packed in the reactor and a fluorocarbon mixture (cell drain product) having a perfluoro-(3-piperizinopropionyl fluoride) content of 61.0% was used as a raw material and the reaction temperature was changed to 200° C.

When 13.49 g of the fluorocarbon mixture was supplied to the reactor and thermally decomposed therein over a period of 60 minutes, there was obtained 8.53 g of fluorocarbon was obtained in the cooled trap.

When this fluorocarbon was analyzed in the same manner as in Example 1, it was found to contain 4.85 g of perfluoro-(N-vinylpiperidine).

The conversion was 100% and the yield 70.2%.

EXAMPLE 7

In the same reactor as used in Example 3, the procedure of Example 5 was repeated, except that 87.5 g of powdered sodium carbonate was packed in the reactor and the product (cell drain product) obtained by electrolytically fluorinating methyl 3-hexamethyleneiminopropionate was used as a raw material, and the reaction temperature was changed to 220° C. The product mentioned above was found to contain 17.7% by weight of perfluoro-(3-hexamethyleneiminopropionyl fluoride) and 18.5% by weight of perfluoro-[3-(methylpiperazino)-propionyl fluoride), an isomer.

When 12.49 g of the flurocarbon mixture was supplied to the reaction and thermally decomposed therein over a period of 45 minutes, there was obtained 7.69 g of fluorocarbon as condensed in the cooled trap.

When this fluorocarbon was analyzed in the same manner as in Example 1, it was found to contain 1.68 g of perfluoro-(N-vinylhexamethyleneimine) and 1.69 g of perfluoro-[N-vinyl(methylpiperazine)] (boiling point 102°–103° C.).

The conversion was 100% and the yield of perfluoro-N-vinylhexamethyleneimine) was 88.5% based on the perfluoro-(3-hexamethyleneiminopropionyl fluoride) supplied initially.

What is claimed is:

1. A method for the production of a perfluoro(N-vinylamine) compound having the formula:

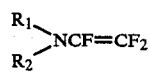

from a perfluoro-compound of the formula:

wherein X is a member selected from the group consisting of fluorine and —OM, wherein M is an alkali metal ion or an alkaline earth metal ion and groups $R_1$ and $R_2$ are perfluoroalkyl groups having a total carbon atom content of 2 to 6 carbon atoms or groups $R_1$ and $R_2$ together form a cyclic perfluorocarbon ring system containing from 2 to 6 carbon atoms within the ring by bonding of $R_1$ and $R_2$ directly together or through an intervening oxygen or nitrogen atom, comprising:

heating said perfluoro-compound at a temperature within the range of 100° C. to 500° C. thereby converting said perfluoro-compound into said perfluoro (N-vinylamine) compound.

2. The method of claim 1, wherein said perfluoro-carbon compound has the formula:

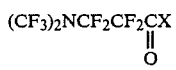

and said perfluoro-(N-vinylamine) compound is vinyldi(trifluoromethyl)amine.

3. The method of claim 1, wherein said perfluorocompound has the formula:

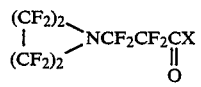

and said perfluoro-(N-vinylamine) compound has the formula:

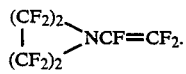

4. The method of claim 1, wherein said perfluorocompound has the formula:

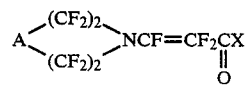

wherein A is a member selected from the group consisting of —$CF_2$—, —O—, and =$NC_nF_{2n+1}$, wherein n is an integer within the range of 1 to 5 and said perfluoro-(N-vinylamine) compound has the formula:

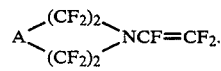

5. The method of claim 1, wherein said perfluorocompound has the formula:

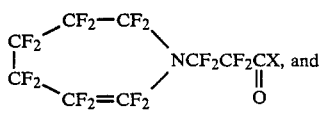

said perfluoro-(N-vinylamine) compound has the formula:

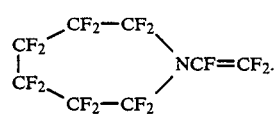

6. The method of claim 1, wherein said perfluorocompound has the formula:

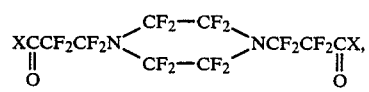

and said perfluoro-(N-vinylamine) compound as the formula:

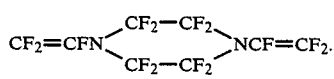

* * * * *